United States Patent
Berenyi et al.

(10) Patent No.: US 11,452,862 B2
(45) Date of Patent: Sep. 27, 2022

(54) INTERSECTIONAL SHORT-PULSE ELECTRICAL STIMULATION OF THE BRAIN

(71) Applicants: NEW YORK UNIVERSITY, New York, NY (US); UNIVERSITY OF SZEGED, Szeged (HU)

(72) Inventors: Antal Berenyi, Szeged (HU); Gyorgy Buzsaki, Maplewood, NJ (US)

(73) Assignees: New York University, New York, NY (US); University of Szeged, Szeged (HU)

(*) Notice: Subject to any disclaimer, the term of this patent is extended or adjusted under 35 U.S.C. 154(b) by 387 days.

(21) Appl. No.: 16/613,400

(22) PCT Filed: May 17, 2018

(86) PCT No.: PCT/US2018/033253
§ 371 (c)(1),
(2) Date: Nov. 13, 2019

(87) PCT Pub. No.: WO2018/213622
PCT Pub. Date: Nov. 22, 2018

(65) Prior Publication Data
US 2020/0164201 A1 May 28, 2020

Related U.S. Application Data

(60) Provisional application No. 62/508,251, filed on May 18, 2017.

(51) Int. Cl.
*A61N 1/04* (2006.01)
*A61N 1/36* (2006.01)
*A61B 5/377* (2021.01)

(52) U.S. Cl.
CPC ........ *A61N 1/0456* (2013.01); *A61N 1/0476* (2013.01); *A61N 1/3603* (2017.08); *A61N 1/36025* (2013.01); *A61B 5/377* (2021.01)

(58) Field of Classification Search
None
See application file for complete search history.

(56) References Cited

U.S. PATENT DOCUMENTS 7,917,221 B2  3/2011  Tass
8,612,018 B2  12/2013  Gillbe
(Continued)

FOREIGN PATENT DOCUMENTS

| JP | 2014-502900 A | 2/2014 |
| WO | WO-2010/100643 A2 | 9/2010 |
| WO | WO-2016/057855 A1 | 4/2016 |

OTHER PUBLICATIONS

Adrian & Matthews, "The interpretation of potential waves in the cortex," The Journal of Physiology 81(4), pp. 440-471 (1934).
(Continued)

*Primary Examiner* — Michael W Kahelin
(74) *Attorney, Agent, or Firm* — Foley & Lardner LLP

(57) ABSTRACT

A system for electrical brain stimulation including a plurality of electrodes arranged around the patient's brain (either directly or indirectly through layers of dura, skull or skin) such that axes connecting each electrode pair intersect at a predetermined focal point, and a ground-independent switching circuit configured to selectively activate and deactivate electrodes via a plurality of ground-independent switches. Electrodes are sequentially activated and deactivated.

20 Claims, 6 Drawing Sheets

(56) References Cited

U.S. PATENT DOCUMENTS

| | | | |
|---|---|---|---|
| 2006/0106430 A1 | 5/2006 | Fowler et al. | |
| 2011/0077717 A1* | 3/2011 | Poletto | A61N 1/3616 607/66 |
| 2015/0174418 A1 | 6/2015 | Tyler et al. | |
| 2016/0082251 A1 | 3/2016 | Moffitt et al. | |
| 2016/0136427 A1* | 5/2016 | De Ridder | A61N 1/36139 607/45 |
| 2016/0228178 A1* | 8/2016 | Lei | A61N 1/06 |

OTHER PUBLICATIONS

Agnew & McCreery, "Considerations for safety in the use of extracranial stimulation for motor evoked potentials," Neurosurgery 20(1), pp. 143-147 (1987).
Akhtari, et al., "Conductivities of Three-Layer Live Human Skull," Brain Topography 14, pp. 151-167 (2002).
Amzica & Massimini, "Glial and Neuronal Interactions during Slow Wave and Paroxysmal Activities in the Neocortex," Cerebral Cortex 12(10), pp. 1101-1113 (2002).
Anastassiou, et al., "The Effect of Spatially Inhomogeneous Extracellular Electric Fields on Neurons," Journal of Neuroscience 30(5), pp. 1925-1936 (2010).
Antal & Paulus, "Investigating Neuroplastic Changes in the Human Brain Induced by Transcranial Direct (tDCS) and Alternating Current (tACS) Stimulation Methods," Clinical EEG and Neuroscience 43(3), p. 175 (2012).
Antal & Paulus, "Transcranial alternating current stimulation (tACS)," Frontiers in Human Neuroscience 7, 317, 4 pages (2013).
Baseler, et al., "The topography of visual evoked response properties across the visual field," Electroencephalography and Clinical Neurophysiology 90(1), pp. 65-81 (1994).
Berenyi, et al., "Closed-Loop Control of Epilepsy by Transcranial Electrical Stimulation," Science 337(6095), pp. 735-737 (2012).
Bikson, et al., "Effects of uniform extracellular DC electric fields on excitability in rat hippocampal slices in vitro," The Journal of Physiology 557(1), pp. 175-190 (2004).
Bikson, et al., "Electrode montages for tDCS and weak transcranial electrical stimulation: Role of "return" electrode's position and size," Clinical Neurophysiology 121(12), pp. 1976-1978 (2010).
Bindman, et al., "The action of brief polarizing currents on the cerebral cortex of the rat (1) during current flow and (2) in the production of long-lasting after-effects," The Journal of Physiology 172(3), pp. 369-382 (1964).
Chan & Nicholson, "Modulation by applied electric fields of Purkinje and stellate cell activity in the isolated turtle cerebellum," The Journal of Physiology 371(1), pp. 89-114 (1986).
Datta, et al., "Cranial electrotherapy stimulation and transcranial pulsed current stimulation: A computer based high-resolution modeling study," NeuroImage 65, pp. 280-287 (2013).
Datta, et al., "Gyri-precise head model of transcranial direct current stimulation: Improved spatial focality using a ring electrode versus conventional rectangular pad," Brain Stimulation 2(4), pp. 201-207 (2009).
Dmochowski, et al., "The point spread function of the human head and its implications for transcranial current stimulation," Physics in Medicine & Biology 57(20), pp. 6459-6477 (2012).
Extended European Search Report for European Patent App. No. 18803289.0 dated Nov. 13, 2020, 7 pages.
Faria, et al., "A finite element analysis of the effect of electrode area and inter-electrode distance on the spatial distribution of the current density in tDCS," Journal of Neural Engineering 8(6), 066017, 24 pages (2011).
Fertonani, et al., "What do you feel if I apply transcranial electric stimulation? Safety, sensations and secondary induced effects," Clinical Neurophysiology 126(11), pp. 2181-2188 (2015).
Friedberg, et al., "Modulation of Receptive Field Properties of Thalamic Somatosensory Neurons by the Depth of Anesthesia," Journal of Neurophysiology 81(5), pp. 2243-2252 (1999).
Frohlich & McCormick, "Endogenous Electric Fields May Guide Neocortical Network Activity," Neuron 67(1), pp. 129-143 (2010).
Frohlich & Schmidt, "Rational design of transcranial current stimulation (TCS) through mechanistic insights into cortical network dynamics," Frontiers in Human Neuroscience 7, 804, 5 pages (2013).
Geisler & Goldberg, "A Stochastic Model of the Repetitive Activity of Neurons," Biophysical Journal 6(1), pp. 53-69 (1966).
Hazan, et al., "Klusters, NeuroScope, NDManager: A free software suite for neurophysiological data processing and visualization," Journal of Neuroscience Methods 155(2), pp. 207-216 (2006).
Hood, et al., "The Multifocal Visual Evoked Potential," Journal of Neuro-Ophthalmology 23(4), pp. 279-289 (2003).
Horvath, et al., "Quantitative Review Finds No Evidence of Cognitive Effects in Healthy Populations From Single-session Transcranial Direct Current Stimulation (tDCS)," Brain Stimulation 8(3), pp. 535-550 (2015).
Iyer, et al., "Safety and cognitive effect of frontal DC brain polarization in healthy individuals," Neurology 64(5), pp. 872-875 (2005).
Jefferys, "Nonsynaptic modulation of neuronal activity in the brain: electric currents and extracellular ions," Physiological Reviews 75(4), pp. 689-723 (1995).
Kanai, et al., "Frequency-Dependent Electrical Stimulation of the Visual Cortex," Current Biology 18(23), pp. 1839-1843 (2008).
Latikka, et al., "The conductivity of brain tissues: comparison of results in vivo and in vitro measurements," Proceedings of the 23rd Annual International Conference of the IEEE Engineering in Medicine and Biology Society, 3 pages (2001).
Leksell, "The stereotactic method and radiosurgery of the brain," Acta Chirurgica 102, pp. 316-319 (1951).
Liebetanz, et al., "Safety limits of cathodal transcranial direct current stimulation in rats," Clinical Neurophysiology 120(6), pp. 1161-1167 (2009).
Logothetis, et al., "In Vivo Measurement of Cortical Impedance Spectrum in Monkeys: Implications for Signal Propagation," Neuron 55(5), pp. 809-823 (2007).
Margrie, et al., "In vivo, low-resistance, whole-cell recordings from neurons in the anaesthetized and awake mammalian brain," Pflugers Archiv-13 European Journal of Physiology 444, pp. 491-498 (2002).
Marshall & Binder, "Contribution of transcranial oscillatory stimulation to research on neural networks: an emphasis on hippocampo-neocortical rhythms," Frontiers in Human Neuroscience 7, 614, 6 pages (2013).
Marshall, et al., "Boosting slow oscillations during sleep potentiates memory," Nature 444, pp. 610-613 (2006).
Marshall, et al., "Transcranial Direct Current Stimulation during Sleep Improves Declarative Memory," Journal of Neuroscience 24(44), pp. 9985-9992 (2004).
Merton & Morton, "Stimulation of the cerebral cortex in the intact human subject," Nature 285, p. 277 (1980).
Monai, et al., "Calcium imaging reveals glial involvement in transcranial direct current stimulation-induced plasticity in mouse brain," Nature Communications 7, 11100, 10 pages (2016).
Nitsche & Paulus, "Excitability changes induced in the human motor cortex by weak transcranial direct current stimulation," The Journal of Physiology 527(3), pp. 633-639 (2000).
Nitsche, et al., "Transcranial direct current stimulation: State of the art 2008," Brain Stimulation 1(3), pp. 206-223 (2008).
Ozen, et al., "Transcranial Electric Stimulation Entrains Cortical Neuronal Populations in Rats," Journal of Neuroscience 30(34), pp. 11476-11485 (2010).
Paulus, "On the difficulties of separating retinal from cortical origins or phosphenes when using transcranial alternating current stimulation (tacs)," Clinical Neurophysiology 121(7), pp. 987-991 (2010).
Pogosyan, et al., "Boosting Cortical Activity at Beta-Band Frequencies Slows Movement in Humans," Current Biology 19(19), pp. 1637-1641 (2009).
Priori, "Brain polarization in humans: a reappraisal of an old tool for prolonged non-invasive modulation of brain excitability," Clinical Neruophysiology 114(4), pp. 589-595 (2003).

(56) References Cited

OTHER PUBLICATIONS

Purpura & McMurtry, "Intracellular Activities and Evoked Potential Changes During Polarization of Motor Cortex," Journal of Neurophysiology 28(1), pp. 166-185 (1965).
Radman, et al., "Role of cortical cell type and morphology in subthreshold and suprathreshold uniform electric field stimulation in vitro," Brain Stimulation 2(4), pp. 215-228 (2009).
Ranck, "Which elements are excited in electrical stimulation of mammalian central nervous system: A review," Brain Research 98(3), pp. 417-440 (1975).
Reato, et al., "Low-Intensity Electrical Stimulation Affects Network Dynamics by Modulating Population Rate and Spike Timing," Journal of Neuroscience 30(45), pp. 15067-15079 (2010).
Reato, et al., "Transcranial Electrical Stimulation Accelerates Human Sleep Homeostasis," PLOS Computational Biology 9(2), e1002898, 13 pages (2013).
Rossant, et al., "Spike sorting for large, dense electrode arrays," Nature Neuroscience 19, pp. 634-641 (2016).
Ruohonen & Karhu, "tDCS possibly stimulates glial cells," Clinical Neurophysiology 123(10), pp. 2006-2009 (2012).
Schomburg, et al., "Theta Phase Segregation of Input-Specific Gamma Patterns in Entorhinal-Hippocampal Networks," Neuron 84(2), pp. 470-485 (2014).
Schutter & Hortensius, "Retinal origin of phosphenes to transcranial alternating current stimulation," Clinical Neurophysiology 121(7), pp. 1080-1084 (2010).
Schwiedrzik, "Retina or visual cortex? The site of phosphene induction by transcranial alternating current stimulation," Frontiers in Integrative Neuroscience 3, 6, 2 pages (2009).
Tort, et al., "Measuring Phase-Amplitude Coupling Between Neuronal Oscillations of Different Frequencies," Journal of Neurophysiology 104(2), pp. 1195-1210 (2010).
Tranchina & Nicholson, "A model for the polarization of neurons by extrinsically applied electric fields," Biophysical Journal 50(6), pp. 1139-1156 (1986).
Tyler, et al., "Transdermal neuromodulation of noradrenergic activity suppresses psychophysiological and biochemical stress responses in humans," Scientific Reports 5, 13865, 17 pages (2015).
Vass, "The elusive universal post-mortem interval formula," Forensic Science International 204(1-3), pp. 34-40 (2011).
Wagner, et al., "Three-dimensional head model Simulation of transcranial magnetic stimulation," IEEE Transactions on Biomedical Engineering 51(9), pp. 1586-1598 (2004).
Watanabe, et al., "Transcranial electrical stimulation through screw electrodes for intraoperative monitoring of motor evoked potentials," Journal of Neurosurgery 100(1), pp. 155-160 (2004).
Wendel & Malmivuo, "Correlation between Live and Post Mortem Skull Conductivity Measurements," International Conference of the IEEE Engineering in Medicine and Biology Society, pp. 4285-4288 (2006).
Zaghi, et al., "Noninvasive Brain Stimulation with Low-Intensity Electrical Currents: Putative Mechanisms of Action for Direct and Alternating Current Stimulation," The Neuroscientist 16(3), pp. 285-307 (2010).
Zheng, et al., "Impedance of Skeletal Muscle from 1 Hz to 1 MHz," IEEE Transactions on Biomedical Engineering BME-31(6), pp. 477-481 (1984).
Grossman, N., et al., "Noninvasive Deep Drain Stimulation via Temporally Interfering Electric Fields", Cell, Jun. 1, 2017, 169:1029-1041.
International Search Report and Written Opinion in PCT/US2018/033253, dated Aug. 7, 2018, 7 pages.
Official Action for JP Patent App. No. 2020-514143 dated Jan. 17, 2022, 4 pages (with English translation).

* cited by examiner

INTERSECTIONAL SHORT-PULSE ELECTRICAL STIMULATION OF THE BRAIN

CROSS-REFERENCE TO RELATED APPLICATIONS

This application is the U.S. national phase of International Application No. PCT/US2018/033253 filed May 17, 2018, which claims priority benefit of U.S. Provisional Application No. 62/508,251, filed May 18, 2017, both of which are incorporated herein by reference in their entirety for all purposes.

TECHNICAL FIELD

The present disclosure relates generally to a system and method for transcranial electrical stimulation. More specifically, the present disclosure relates to a system and method of intersectional short pulse electrical stimulation for interacting with neuronal and/or glial activity in a spatially and/or temporally selective manner.

BACKGROUND

Neuropsychiatric disorders may be exacerbated due to pathologic changes in the oscillatory processes of the brain. Most therapeutic interventions aim to restore physiological activity patterns. In pharmacological approaches, patients take drugs that act on the central nervous system. As an additional or alternative approach to the pharmacological approach, brain activity can be modified by externally generated electrical fields in an electrical modulation approach. An advantage of the electrical modulation approach over the pharmacological approach is that electric fields build up and break down instantaneously. Thus, the effect of electrical stimulation can be precisely timed with no adverse effects during the non-stimulated periods.

Currently there are three ways to affect activity of neuronal circuits by using electrical or magnetic approaches. The first approach, deep brain stimulation, is an invasive approach in which electrical current is locally delivered to targeted area(s) of the brain via electrodes implanted into the brain tissue. The second approach, transcranial magnetic stimulation, is a noninvasive procedure that uses magnetic fields to induce electrical currents, and thus indirectly stimulate nerve cells in the brain. Transcranial magnetic stimulation can be challenging because the apparatus used to generate the magnetic fields cannot be arbitrarily miniaturized, since the coils inducing the magnetic fields have certain minimal size requirements due to the constraints of physics. Lastly, the third approach, electrical stimulation, is a noninvasive or minimally invasive procedure that uses electric fields to stimulate nerve cells in the brain. In noninvasive electrical stimulation procedures, electrodes are epicutaneous, while in minimally invasive electrical stimulation procedures, electrodes are subcutaneous. These approaches are considered to be noninvasive or minimally invasive in that the stimulating electrodes are implanted on the skin or skull surface, the latter requiring an incision to be made in the skin, but none of them disrupt the integrity of the skull i.e. by making a craniotomy. Electrical stimulation can be challenging because the small electrodes applied to the skin/skull can only induce relatively diffuse, untargeted effects in the brain. In electrical stimulation approaches, various stimulus waveforms may be used such as direct current, alternating current and random noise. Examples of electrical stimulation approaches include, but not limited to, transcranial electrical stimulation (TES), transcutaneous (scalp) direct current stimulation (tDCS), transcutaneous (transcranial) alternating current stimulation (tACS) and transcutaneous (transcranial) random noise stimulation (tRNS). To avoid the ambiguity of the terminology, non-invasive approaches using electrodes placed on the outer surface of the skin are referred to as transcutaneous-transcranial electrical stimulation (tcTES) with no respect to the applied waveform. Similarly, minimal-invasive approaches where the electrodes are placed below the skin, either onto the outer surface of the skull or into the outer segments of the skull bone (i.e., into the external compact layer or the spongious layer), leaving the integrity of at least the internal compact layer of the skull intact are named subcutaneous-transcranial electrical stimulation (scTES).

Both transcutaneous direct current stimulation (referred to as tDCS in the literature) and transcutaneous alternating current stimulation (referred to as tACS in the literature) have been extensively used in attempts to affect cognitive behavior and in various forms of brain diseases. Given the lack of direct support for neuronal entrainment in humans, to date, there is no accepted physiological theory how these methods affect cognition or disease. One potential target is to modulate endogenous brain oscillations. However, electrical stimulation of the scalp can affect brain activity in multiple indirect ways, including activation of afferent nerves, retina and the vestibular apparatus, astrocytes and perivascular elements other possible unknown ways and placebo effects. For many therapeutic applications, it would be desirable to affect neurons directly and in a regionally constrained manner to reach immediately and reproducibly maximum on-target effects and reduce side effects on unintended brain networks. However, achieving targeted effects by scalp-applied currents requires precise knowledge about the spread of electric fields in the human head and exploiting intersectional methods of current applications through multiple electrodes.

Electric fields spreading in the extracellular space, generated either by neurons themselves or applied externally, can affect the transmembrane potential of neurons and, consequently, the probability of occurrence of action potentials. Forced electric fields, induced either locally (e.g., in deep brain stimulation) or non-invasively/minimally invasively through the scalp, can be exploited to affect brain activity in humans for both probing the physiological patterns in the brain and, potentially, to ameliorate brain disease.

Ample experimental evidence demonstrates that sufficient magnitude of electric fields can affect both membrane potential ($V_m$) and spiking of neurons. Such ephaptic effects depend on the combination of the morphology, biophysical properties and dendritic orientation of the neurons relative to the electric field dipole. In vitro experiments and computational modeling suggest that the voltage gradient of the induced electric dipole field should exceed 1 mV/mm to generate observable neuronal responses. In vivo, threshold estimation is more complex since endogenous $V_m$ fluctuation (e.g. due to synaptic inputs, or the internal dynamics of the cell) and the ephaptic effects can summate or subtract. In principle, even extremely weak ephaptic forcing of the $V_m$ may entrain networks of neurons when applied at the right state of the network, e.g., at the appropriate phase of neuronal oscillations. Measurements in behaving animals demonstrate that transcranially applied currents can induce phase-locked firing of neurons in both neocortex and hippocampus, affect subthreshold $V_m$ as measured intracellularly or indirectly by the amplitude of local field potentials (LFP). In summary, there is a consensus from laboratory experiments that sufficient magnitude fields in brain tissue can consistently affect neuronal groups.

It has been hypothesized that electrical stimulation of the scalp can bias or entrain native networks in the human brain. However, the translation of animal results to humans is complicated by unknown properties of the skin, subcutaneous soft tissue, skull, cerebrospinal fluid and brain folding on current spread. Strong stimulations (>50 mA; 0.5 ms pulses) through intracranial screw electrodes in anesthetized patients showed convincing brain network-induced effects. Up until recently there was no means by which to justify a given intensity range to induce reliable neuronal effects, due to the absence of methods to simultaneously stimulate and record brain activity without distortion. Consequently the estimates of the minimum current applied to the scalp to generate the desired voltage gradient in the human brain vary greatly, and in most clinical and experimental studies, a maximum of 1 to 2 mA current has been used due to safety considerations and to reduce peripherally evoked sensory effects. Recently, direct electrical field measurements in the brains of human cadavers revealed, that the electrical shunting effect of the human scalp and skull is larger than previously estimated. The presence of the skull attenuates approximately 25% of the intracerebral electrical gradient compared to stimulating directly on the brain surface, which is further reduced by another 50% if the scalp and subcutaneous soft tissue were present as well. These measurements established the need of a minimum of 5 mA stimulus current to reliably and immediately command the activity of selected brain regions, which immediate effect is desired in many applications (e.g. quickly terminating epileptic seizures immediately after they start).

In order to generate electric fields of at least 1 mV/mm strength at the targeted area, non-invasive, epicutaneous electrodes may be aligned on the scalp surface and used with a 5 mA or more current intensity. In order to generate electric fields of at least 1 mV/mm strength at the targeted area, minimally-invasive, subcutaneous electrodes may be aligned on the skull surface and used with a 2 mA or more current intensity. However, both of these approaches are challenging because the application of 2 mA current for more than a few tens of seconds causes serious adverse effects at the electrode-skin contact sites due to the local stimulation of the skin and in the subcutaneous tissues. In particular, the application of >2 mA currents for durations reasonably long enough to interact with endogenous network activity (i.e. tens to hundreds of milliseconds minimum) using the existing transcranial stimulation protocols are not easily tolerable by the patients due to the adverse skin effects (e.g. itching, burning feeling, pain), phosphenes (sparks) in vision due to stimulation of the retina and dizziness due to stimulation of the vestibular apparatus generated by the large electrical gradients in the close vicinity of the electrodes. Thus, a 5 mA or more intensity (for noninvasive, epicutaneous electrodes) is not tolerable or possible with the conventional approaches, and a 2 mA or more intensity (for minimally invasive, subcutaneous electrodes) is difficult with the conventional approaches. Traditional electrical stimulation approaches using 2 mA current or less are likely to act through non-neuronal ways, and have only postponed effects after cumulating during long stimulation periods. Thus, this approach is not suitable for use in immediate interventions, e.g., to quickly terminate epileptic seizures. Invasive electrode alignments into or under the skull may allow reaching the 1 mV/mm intracerebral electric field strength by even smaller currents, however this requires major surgical intervention by opening the skull.

A need exists for improved technology to develop a non-invasive or minimal-invasive approach to interact with neuronal activity in a spatially and temporally selective manner.

SUMMARY

Various embodiments relate to a system for electrical brain stimulation including a plurality of electrodes arranged. The plurality of electrode pairs are arranged in a plurality of electrode groups. Each electrode group includes two or more electrodes where at least one electrode is set to a different potential level than another electrode such that a voltage difference is generated between members of an electrode group. The electrode are arranged on one of on an exterior surface of a patient's scalp (noninvasive), an exterior surface of a patient's skull (minimally invasive), in the patient's skull, on the patient's brain or dura surface, or in the patient's brain (invasive). The system further includes a ground-independent switching circuit configured to selectively activate and deactivate electrode groups via at least one ground-independent switch. Axes connecting electrodes set to different potential levels within each electrode group or axes of generated electrical fields intersect at one or more predetermined focal points. The ground-independent switching circuit is programmed to sequentially activate and deactivate electrode groups. The system utilizes the capacitive properties of neuronal and/or glial cell membranes to implement a charge integrating mechanism, which temporally integrates an effect of multiple independent, sequential electrical pulses delivered through the two or more activated electrodes.

In some aspects of the system, each electrode in the plurality of electrodes is a member of one or more electrode groups.

In some aspects of the system, each electrode in the plurality of electrodes is only a member of one electrode group.

In some aspects of the system, a cycle comprises one activation and one deactivation of each electrode in an electrode group, and a duration of the cycle is 1 to 100 milliseconds.

In some aspects of the system, each electrode group is activated for shorter than 3.5 ms.

In some aspects of the system, a pause time between consecutive reactivations of any electrode groups is at least twice as long as the duration of its preceding activation.

In some aspects of the system, a plurality of high-intensity pulses is perceived by any cell of brain tissue as a smooth, continuous integrative stimulus at the focal point, due to the capacitive properties and consequent temporal integration (also known as temporal summation) of the neuronal and/or glial cell membrane.

In some aspects of the system, a plurality of high-intensity pulses is perceived by any cell of brain tissue as a smooth, continuous integrative stimulus at the focal point, due to the capacitive properties and consequent temporal integration of the neuronal and/or glial cell membrane via a charge accumulation mechanism.

In some aspects of the system, a cycle comprises one activation and one deactivation of each electrode in an electrode group, and a duration of the cycle is less than a time constant of the neuronal and/or glial cell membrane.

In some aspects of the system, the ground-independent switching circuit comprises the at least one ground-independent switch, which is configured to connect or disconnect two or more signal lines, at least one diode, and a commanding circuit configured to drive the at least one ground-independent switch.

In some aspects of the system, the at least one ground-independent switch comprises a phototransistor.

In some aspects of the system, the ground-independent switching circuit comprises a plurality of ground-independent switches configured to connect or disconnect two or more signal lines, a plurality of diodes, and a commanding circuit configured to drive the plurality of ground-independent switches. The plurality of ground-independent switches comprise a plurality of phototransistors. Each electrode pole is connected to a collector-emitter connection of two serially connected phototransistors.

In some aspects of the system, the plurality of electrodes comprise a plurality of small surface electrodes.

In some aspects of the system, the plurality of electrodes comprise a plurality of large sponge electrodes.

In some aspects of the system, the system further comprises a current or voltage source.

In some aspects of the system, an electrode group comprises an electrode pair in which two electrodes are configured such that a first electrode is physically connected either temporarily or constantly to one pole of the current or voltage source, and a second pole is connected to a second pole of the current or voltage source.

Other embodiments relate to a method of electrical brain stimulation including arranging a plurality of electrodes on an exterior surface of a patient's scalp (noninvasive), an exterior surface of the patient's skull (minimally invasive), in the patient's skull, on the patient's brain or dura surface, or in the patient's brain (invasive) in a plurality of electrode groups and selectively activating and deactivating electrode groups via at least one ground-independent switch. Each electrode group includes two or more electrodes where at least one electrode is set to a different potential level than another electrode such that a voltage difference is generated between members of an electrode group. Axes connecting electrodes set to different potential levels within each electrode group or axes of generated electrical fields intersect at one or more predetermined focal points. Capacitive properties of neuronal and/or glial cell membranes are utilized to implement a charge integrating mechanism, which temporally integrates an effect of multiple independent, sequential electrical pulses delivered through the two or more activated electrodes.

In some aspects of the method, deactivated electrodes are electrically decoupled from a stimulation circuit to avoid shunting an electrical gradient generated by connected active electrodes.

In some aspects of the method, a cycle comprises one activation and one deactivation of each electrode in an electrode group, and a duration of the cycle is less than a time constant of the neuronal and/or glial cell membrane. The time constant of the neuronal and/or glial cell membrane may be ten to forty milliseconds.

In some aspects of the method, each electrode group is activated for shorter than 3.5 ms.

In some aspects of the system or method, electrodes are sequentially activated and deactivated such that at any given time in the procedure, two or more electrodes are activated. In other aspects, electrodes are sequentially activated and deactivated such that at least one time in the procedure, all of the electrodes are deactivated. In further aspects, electrodes are sequentially activated and deactivated such that at least one time in the procedure, all of the electrodes are activated.

The aspects described above are not necessarily mutually exclusive. Two or more of the aspects described above may be combined.

BRIEF DESCRIPTION OF THE DRAWINGS

The details of one or more implementations of the subject matter described in this specification are set forth in the accompanying drawings and the description below. Other features and aspects of the subject matter will become apparent from the description, the drawings, and the claims presented herein.

FIG. 2 illustrates that intersectional short pulse (ISP) stimulation can spatially focus induced fields.

FIG. 3 illustrates that weak currents do not modulate network activity or behavior in human subjects. FIG. 3B illustrates the reaction time (key pressing) after a beep stimulus was not affected by scalp stimulation (P>0.05 for all conditions, n=100 trials per condition, 3 subjects). FIG. 3B illustrates ISP stimulation focused on the left hemisphere (left focus) and right hemisphere (right focus).

FIG. 4 illustrates that high intensity ISP stimulation of the scalp phasically modulates ongoing brain oscillation in human subjects.

FIG. 5 illustrates an equivalent circuit schematic for the application of multiple independent stimulating pairs in an intersectional arrangement activated simultaneously, resembling gamma-ray radiosurgery. Note that due to the common conductive medium, the currents from the two stimulators couple serially, mimicking the effect of one large surface electrode pair and/or increased stimulus intensity, but they don't reach spatial selectivity.

FIG. 6 illustrates that endogenous brain oscillations are modulated by ISP stimulation.

DETAILED DESCRIPTION OF VARIOUS EMBODIMENTS

Figure 1:
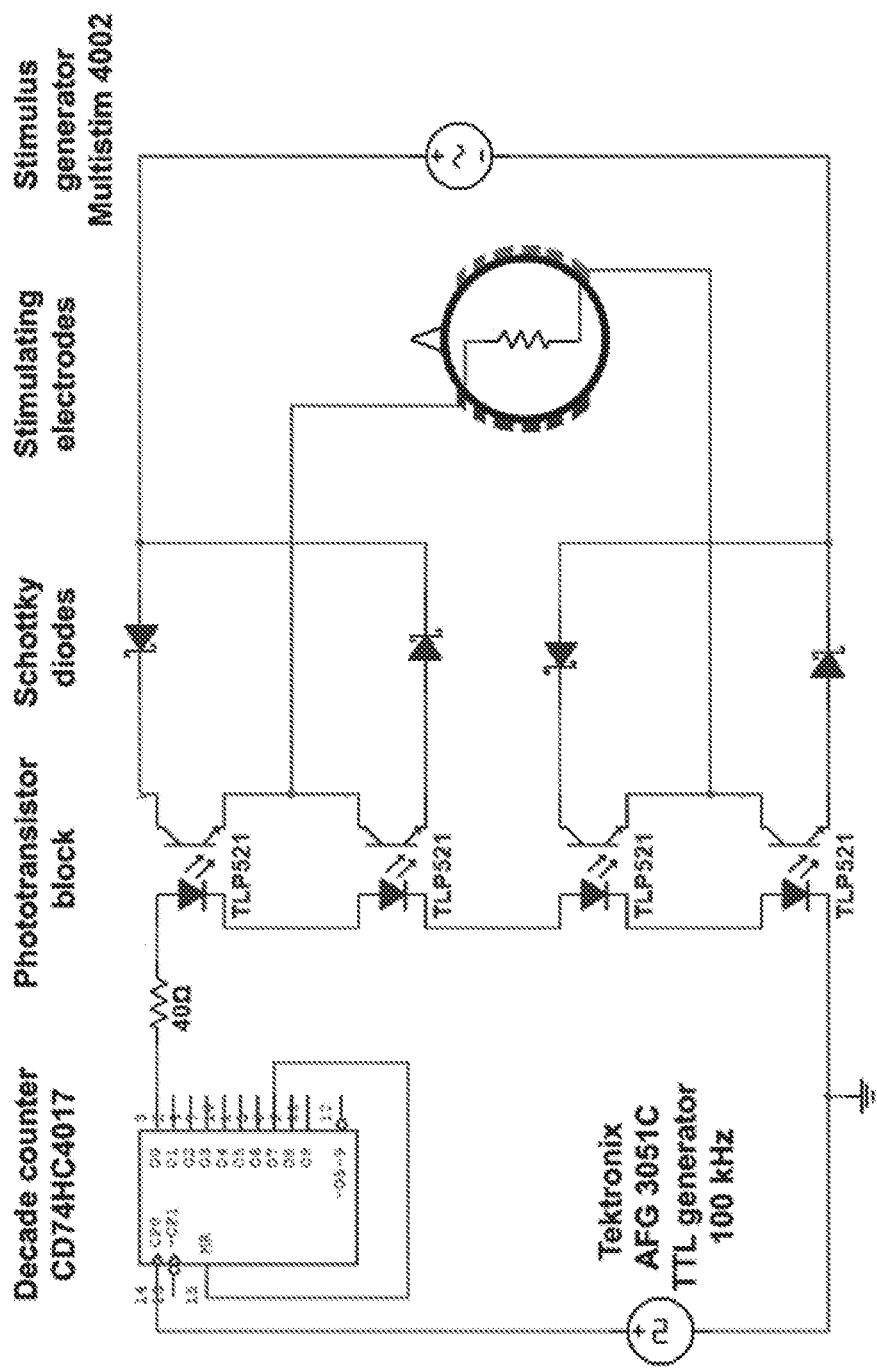
FIG. 1 illustrates an embodiment of a ground-independent switching circuit configured to activate electrode pairs one after the other by using multiple phototransistors driven by a counter integrated circuit. The ground-independent switching circuit is used in a method of intersectional short pulse (ISP) stimulation (i.e., a non-invasive electrical brain stimulation approach).

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring to the figures in general, a system and method for applying current at multiple locations on the scalp/skull/brain is described in the embodiments below. The system or method described in the embodiments below can be used in noninvasive electrical stimulation procedures, where electrodes are epicutaneous, or in minimally invasive electrical stimulation procedures, where electrodes are subcutaneous, or in an invasive way, where electrodes are placed into or under the skull In general, the system includes a plurality of electrodes arranged in multiple locations on the scalp/skull/dura/brain of a patient, where the electrodes are connected to one or more signal sources. The system and methods include transcranial electrical stimulation that utilizes the capacitive properties of neuronal cell membranes to implement a charge integrating mechanism, which temporally integrates the effect of multiple independent, sequential electrical pulses delivered through two or more electrodes. The electrodes may be present in electrode groups comprised of two or more electrodes that are active at the same time in a way that the members (i.e., electrodes) of the electrode group are at different potential levels (i.e., there is a voltage difference generated between members of the electrode groups). In some aspects, an electrode pair refers to at least two electrodes configured such that one or more electrodes are physically connected either temporarily or constantly to one pole of any current or voltage source, while at the same time another one or more electrodes are connected to the other pole. While an electrode group may refer to an electrode pair (i.e., two electrodes), in other examples, an electrode group may be comprised of any number of electrodes (e.g., three, four, five, six, etc.). For example, in a triplet, the electrode group is comprised of three electrodes that are active at the same time in a way that all three electrodes are at a different potential level, or two of them are at the same potential level, while the third one is on a different level. The system and method described in the embodiments below involve electrical stimulation via the plurality of electrodes that utilizes the capacitive properties of neuronal and/or glial cell membranes to implement a charge integrating mechanism, which temporally integrates the effect of multiple independent, sequential electrical pulses delivered through an electrode group comprised of two or more electrodes.

The system and method reduces the peripheral undesired side-effects at the out-of-focus areas, while maintaining high efficacy at the desired focus. In particular, the system and method increase the magnitude of intracerebral fields in a circumscribed target brain volume with non- or minimal-invasive techniques. Due to the constrains deriving from the properties of electric fields, multiple simultaneous stimulation pairs on a common conductive medium cannot maintain the spatial properties of the fields generated by the individual pairs. Thus the integral effect of providing multiple simultaneous stimulation pairs is diffused. The system and method of the present application use intersectional short pulse stimulation to deliver high-intensity (e.g., over 5 mA), yet very short pulses from multiple electrode locations, and utilize the charge-integrating mechanism of the neuronal cell membranes which percept repetitive, fast (e.g., >1 kHz) electrical impulses as a smooth continuous integrative stimulus. Since each electrode is active for only a short duty cycle, the integrative ("apparent") current perceived by the skin under each electrode is distributed between the multiple electrode pairs.

Referring to FIG. 1, one example of a system includes twelve electrodes (six pairs) and a ground-independent switching circuit. The electrodes are arranged on an exterior surface of a patient's scalp or the skull such that axes connecting electrode groups (e.g., electrode pairs) or the axes of the generated electrical fields intersect at one or more predetermined focal points (see FIG. 2B, which illustrates 5 electrode pairs and a focal point represented by a circle). The ground-independent switching circuit is programmed to sequentially activate and deactivate electrode groups such that at any given time in a treatment, a subset of the electrodes is activated (i.e. at least one electrode is set to different potential level than the other members of the same electrode group). For example, the subset may be an electrode group including two or more electrodes. The groups of electrodes are not mutually exclusive, and an electrode can belong to one or more electrode groups. For example, in a case in which there are three electrodes, electrodes 1-6, at a time t1 in the procedure, electrodes 1 and 2 (i.e., Group 1) may be activated. At a time t2 in the procedure, electrodes 2 and 4 (i.e., Group 2) may be activated. In the electrode group, at least one electrode is at a different potential level than another electrode. The remaining electrodes may be on equipotential or each may be at a different potential level than the at least one electrode. All available electrode groups are switched through within a period of time less than a time constant of the neuronal and/or glial membrane. The time constant of the neuronal and/or glial cell membrane is a measurement of how quickly the neuronal and/or glial cell membrane repolarizes after a current injection of fixed amplitude and duration. In other words, the time constant of the neuronal and/or glial membrane is a measurement of how quickly the transmembrane potential level of the neuronal and/or glial cell membrane decays to $1/e^{th}$ (~37%) of the maximum change in the transmembrane potential caused by a current injection of fixed amplitude and duration, compared to the resting transmembrane potential. The time constant is a function of membrane resistance and capacitance, where resistance relates to the type and number of ion channels. The time constant of the neuronal and/or glial cell membrane varies across neuron cell types, but in the in vivo brain it may span an order of magnitude of 10 ms, for example, from 1-100 ms, preferably 5-40 ms, and even more preferably 10-40 ms. In one example, the time constant of the neuronal membrane may be approximately 10 ms, and all available electrode groups may be switched through in less than a millisecond. At any moment, unused (i.e., deactivated) electrodes are electrically decoupled from the stimulation circuit to avoid shunting the electrical gradient generated by the connected active electrodes. Operation of the system is described in further detail below.

The system uses multiple ground-independent switches (e.g. phototransistors) driven by a commanding circuit (e.g., a counter integrated circuit). As used herein, the term "ground-independent switch" refers to any component configured to connect or disconnect two or more signal lines. In one example, the system uses four ground-independent switches in a "block" to preserve bidirectional conductance for bipolar stimulation. In an example in which the ground-independent switches are phototransistors, each electrode pole is connected to a collector-emitter connection of two serially connected phototransistors. The collector of the first phototransistor is connected to the cathode, and the emitter of the second phototransistor is connected to the anode of two diodes (e.g., Schottky diodes). The other pole of the diodes is connected together to one pole of the stimulus generator. This way the positive range of the stimulus waveform is conducted through the first diode-transistor pair while the second diode blocks the conduction toward the second transistor. For the negative range, the conduction happens oppositely: the second diode-transistor block is conducting, while the first diode-transistor block has high resistance. For the other stimulus pole the same circuit is repeated. The LED parts of the four phototransistors belonging to one stimulating electrode pair are activated simultaneously by the output of a counter integrated circuit that is driven by any regular clock generators (e.g., any programmable microchip, 555 timer, etc.). Each output of the counter can drive one switching block of four transistors-two diodes, corresponding to one stimulating electrode pair. The concept can also be realized with any other bipolar ground-independent switches, and the locations of the electrodes on the head, the pattern of the electrode group assignments and their activation sequence being determined with respect to the individual variances of the subjects, and the location of the area to be targeted. The stimulus generator can be any ground-independent third party stimulus generator.

The stimulator-side of the circuitry consists of completely passive, ground-independent components, which do not influence the floating character of the stimulus generator used. The counter side of the circuitry contains only low power components at low voltage level, and thus, can be operated by commercially available batteries (i.e., the counter side of the circuitry does not require a high-power power source). In the switching blocks that are not active due to the low voltage level on the corresponding counter legs, the phototransistors are in high-resistance state. Thus, the coupled stimulating electrodes can be considered electrically disconnected. Any arbitrary waveform having a predetermined frequency can be transmitted as the stimulus, which allows the system/method to be used in any type of electrical stimulation (e.g., direct current, alternating current, or random noise).

In the system, a plurality of groups of small surface electrodes are used, as opposed to large sponge electrodes. As used herein, "small surface electrode" refers to an electrode sized to allow placement of a desired number of electrodes, in particular, a minimum of three pairs, on the skull surface in an arrangement that leaves enough space between the pairs to avoid short circuiting. Preferably, a minimum of five to six pairs of electrodes are used. Small electrodes may include electrodes less than 5-by-5 cm, 5 cm diameter, or less than 20 $cm^2$ area. For example, five to six pairs of 2 cm by 2 cm small surface electrodes may be placed on one plane. As used herein "large sponge electrode" refers to an electrode configuration (one pair), or three electrode configurations having a size of 5-10 cm by 5-10 cm, e.g., 5 cm by 5 cm or 10 cm by 10 cm, or comparable sizes. Sponge electrodes are practical for transcutaneous use, as they easily pick up the shape of the head underneath. For subcutaneous (implanted) applications, other electrode types are suitable (e.g. epidural plate electrodes, flexible electrocorticographic electrodes, metal surface electrodes deposited on flexible polymer substrates, metal screw electrodes penetrating the compact part of the skull, etc.). The electrodes are aligned such that the virtual axes determined by those electrode members of the groups which are set to different potential levels during stimulation cross each other at a predetermined focal point, either in one plane or in three dimensions (see FIG. 2B). In one example, 6-8 electrode pairs are used. Using 6-8 electrode pairs causes a theoretical 6-8 fold drop in the apparent intensity at the skin immediately below each electrode if the electrode pairs are located far enough from each other (i.e., a distance that prevents the electrode pairs from touching each other and short-circuiting). However within the brain, at locations where the activity of all of the electrode pairs is present, the apparent current is higher, reaching the desired 1 mV/mm field strength.

Figures 2A, 2C, 2D, 2E:
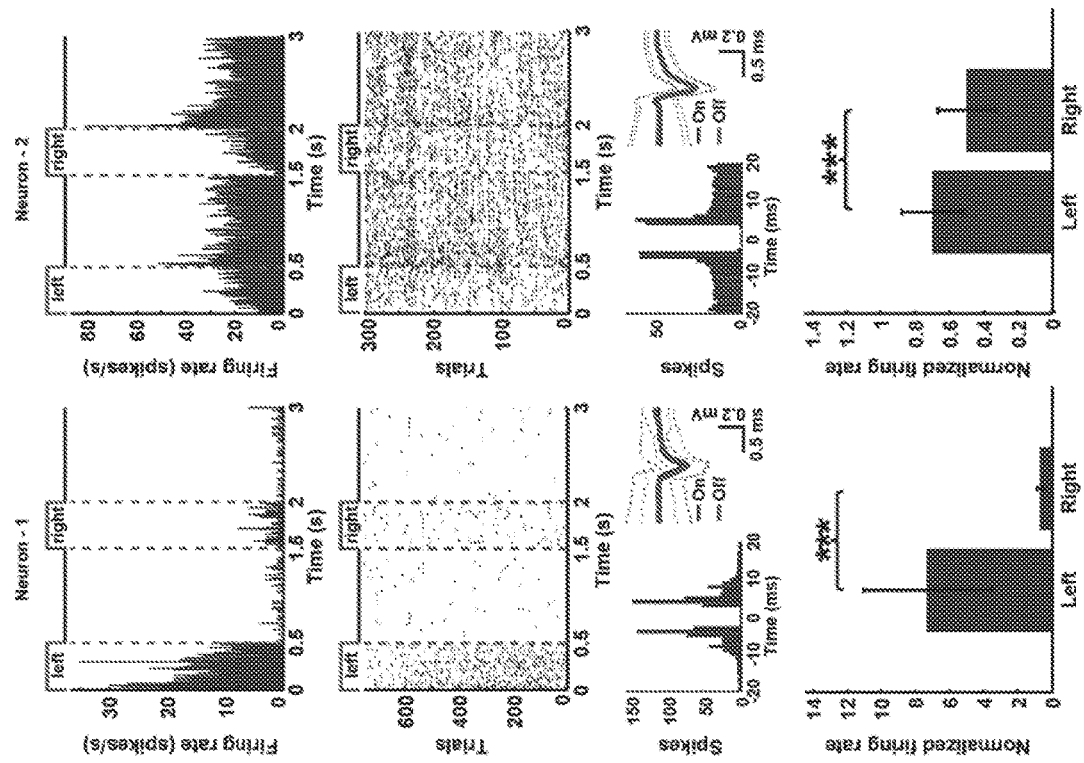
FIG. 2A is a leaky integrate-and-fire neuron model cartoon to demonstrate the concept of ISP stimulation.
FIG. 2C illustrates the activity of two example neurons recorded extracellularly by silicon electrodes while ISP was applied. Neurons were almost selectively entrained (left column) or inhibited (right column) by ipsilateral ISP as shown by their peristimulus time histograms (top panels) and raster plots (middle panels). Artifact free recording of neuronal activity during ISP allowed the reliable isolation of single unit activities as shown by the autocorrelograms during stimulation and the identical spike waveforms during stimulation and control periods.
FIGS. 2D and 2E illustrate 7.6±3.78 vs 2.1±0.59 and 0.59±0.2 vs 0.35±0.15 of the normalized firing rates of entrained (FIG. 2D, n=18 out of 47) and suppressed (FIG. 2E, n=7 out of 47) neurons, demonstrating the lateralized effects of ISP stimulation.

FIG. 2A demonstrates the principle of spatio-temporally rotating intersectional short pulse (ISP) stimulation to spatially focus the effect of transcranial electrical stimulation (TES). Stimulus current is delivered sequentially through three independent electrode pairs generating a continuously changing intracerebral gradient pattern. Neuronal cell membranes can integrate these patterns due to their relatively slow membrane time-constant (approximately 10 ms). Consequently, neurons at the cross section of the current flow axes are cumulating the individual subthreshold effects of all stimuli, and become more strongly entrained than neurons located outside the focus. The method assumes a charge-integrating mechanism over time, exemplified here by a simplified leaky integrate-and-fire neuron model. An added advantage of fast pulses (i.e., at least an order of magnitude shorter compared to the sampling interval of simultaneous neuronal recordings, e.g. 2.5 to 10 μs duty cycle with 5 to 50 μs pause, depending on the number of electrode pairs) is that their high frequency only minimally affects simultaneous electric recording of local field potentials (LFP) or neuronal spikes (1 Hz-5 kHz; 20 kHz sampling) and it does not saturate alternating current coupled recording amplifiers even at relatively high intensities.

Figure 2B:
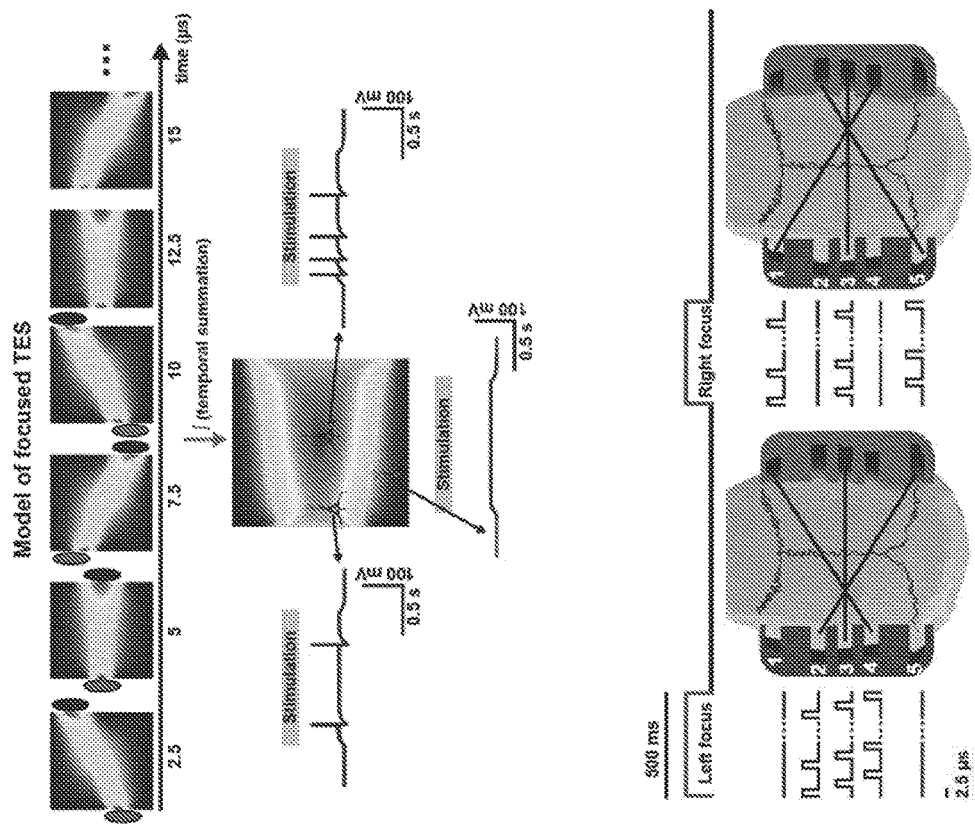
FIG. 2B illustrates an experimental protocol to measure the efficacy of ISP. 3D-printed plastic electrode holders were attached to the temporal bones bilaterally with five gel electrodes on each side. Electrode pairs were programmed to target the ISP beams (intersecting black lines) on either the left or the right hemisphere for 500 ms each, interleaved by non-stimulated control periods. Each electrode pair was pulsed sequentially for 2.5 µs. Extracellular recording electrodes were advanced to the CA1 region of the hippocampus at both sides at the theoretical focal points of the stimulations (circles), and the activity of the neurons at the targeted locations were recorded during stimulation.

To test a model prediction of focal effect in rats, current pulses were delivered in an asymmetric manner through five independently programmable isolated current generators, which were connected to a 3-D printed gel-electrode strip glued to the temporal bone surface (see FIG. 2B). During in vivo recordings of extracellular unit activity in the hippocampal CA1 region, the transcranial bipolar configuration alternated. See FIG. 2B in which included a sequence of 500 ms train of fast rotating pulses focused on the left hemisphere and 1,000 ms off, followed by the same sequence focusing on the right hemisphere). The effectiveness of the ISP stimulation on spatially targeted entrainment of single unit activity is illustrated on two example neurons (FIG. 2C), which increased and decreased their firing rates, respectively, depending on the hemisphere targeted by the ISP stimulation. Due to the very short duration stimulation pulses, single unit spike trains were not contaminated by electrical noise as shown by the similar spike waveforms and spike autocorrelograms during stimulation and stimulation-free periods (FIG. 2C). Overall, the current focusing effect of ISP, using only three rotating dipoles, resulted in an approximately 2 to 1 ratio of excitation gain between left and right hemisphere-focused "beams" as measured by spike occurrence probabilities (FIG. 2D; 7.6±3.78% vs 2.1±0.59% increase; $P<0.005$ for n=18 excited and 0.59±0.2% vs 0.35±0.15% decrease; $P<0.05$ for n=7 suppressed out of 47 recorded neurons in 4 rats; Wilcoxon signed rank test). In other words, the ISP technique allows for generating apparently spatially concentrated electrical fields (from the neurons point of view, not physically) to selectively control activity also in subcortical structures and simultaneous recording of electrical activity.

Entraining Human Brain Network Activity by ISP

Figure 3B:
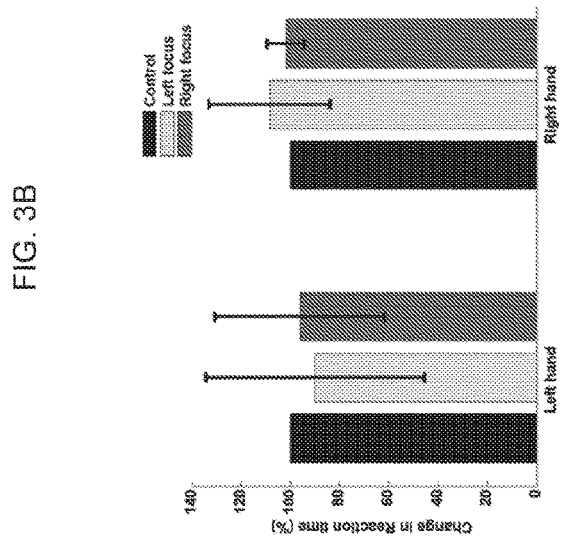
FIGS. 3A and 3B illustrate the effect of 2 mA ISP stimulation on visually evoked potentials and reaction time, respectively. Note the similar waveforms in control and stimulated (TES) sessions (FIG. 3A, P=0.33; n=18 sessions in 2 subjects).
Figure 3D:
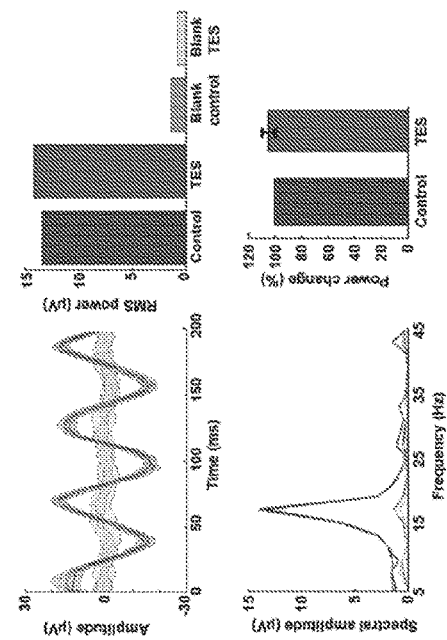
FIG. 3D illustrates that 2 mA tDCS applied through 10×10 cm sponge electrodes had no effect on 17 Hz steady-state visual evoked responses. Note similarity of average response waveforms (top left panel which illustrates stimulated and control sessions), and identical power spectra (bottom left panel). To test whether electromagnetic radiation of the screen might be responsible for the similarity, measurements were repeated by blocking the sight with a cardboard paper (blank control; blank TES: control with no visual stimulation). Root mean square power (top right panel) and power spectral density at 17 Hz (bottom right panel) did not show any significant difference (P=0.62, n=24 sessions; 2 subjects).
Figure 3A:
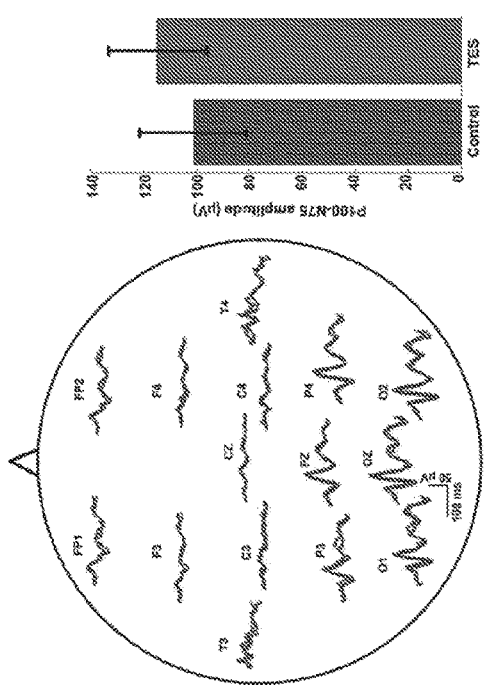
Figure 3C:
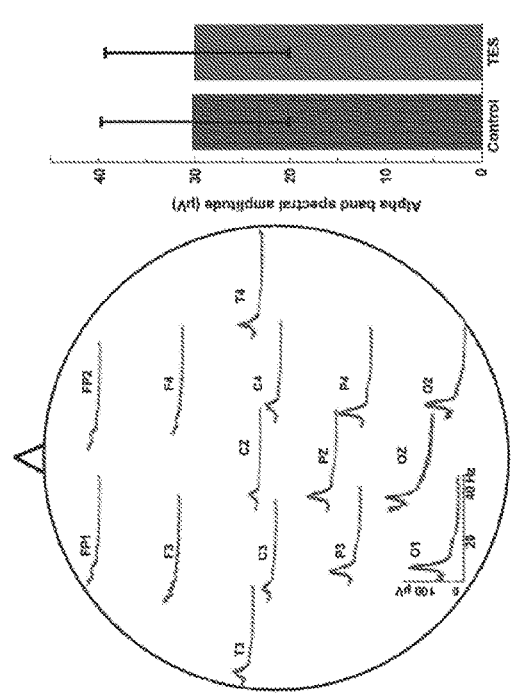
FIG. 3C illustrates that 2 mA tDCS did not affect alpha frequency or amplitude (eyes closed). Left panel: example session; right panel: average of alpha amplitude on occipital leads (P=0.68, n=22 sessions in 2 subjects).
Figure 5:
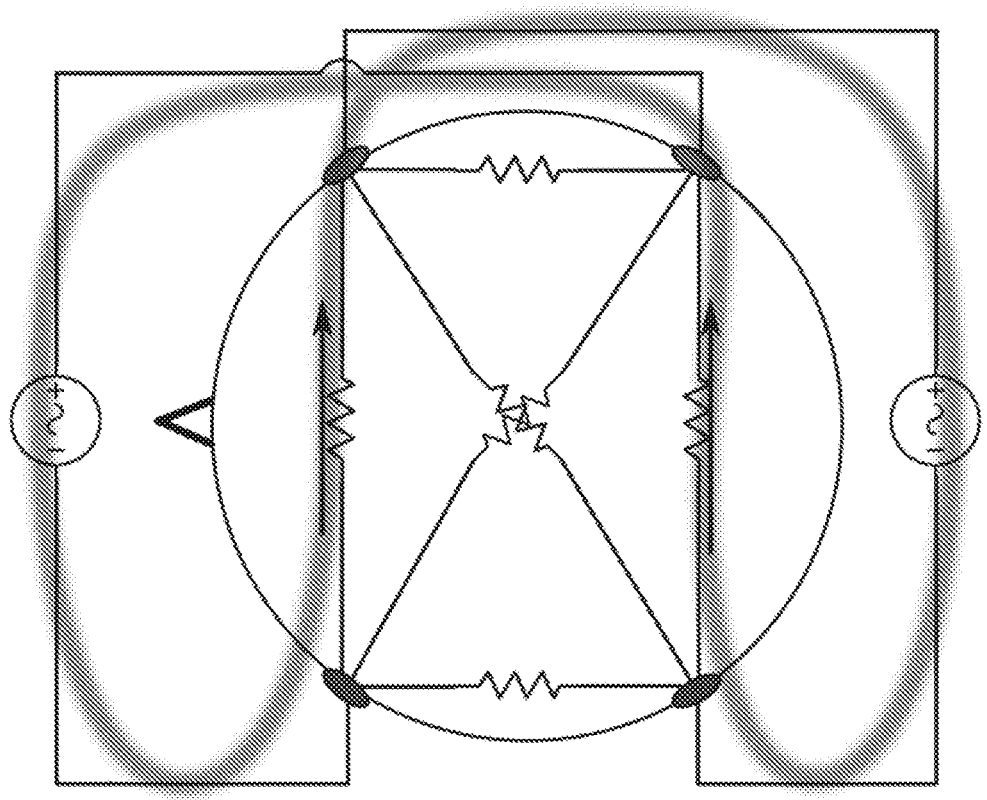
FIG. 5 explains that multiple simultaneous stimulator pairs do not focus the intracerebral electric gradients.

Direct electrical field measurements performed on human cadavers indicated that approximately 5 mA currents applied to the scalp are needed to reach the desired intracerebral voltage gradient (~1 mV/mm), which was shown in other experiments minimally required to instantaneously and reproducibly alter brain networks. To test this prediction, visual evoked potentials and reaction time to auditory stimuli were compared in healthy subjects using both ISP method (FIGS. 3a and 3b) and power spectra of spontaneous brain activity, and rhythmic entrainment of visual networks (steady-state visual evoked potentials) using the traditional tDCS method (either with small or large epicutaneous sponge electrodes; FIGS. 5c and 5d, respectively). In the traditional tDCS method, two sponge electrodes are placed on the scalp on the two sides of the head, and direct current is applied through the electrodes, usually at a 2 mA current intensity. A significant effect of transcutaneous stimulation was not observed with 2 mA current in any of these experiments. Subjects occasionally reported perception of phosphenes (visual "sparks") at either the onset or offset of stimulation. These negative results should be contrasted with the effectiveness of subsequent stronger stimulations on network patterns.

Figure 6A:
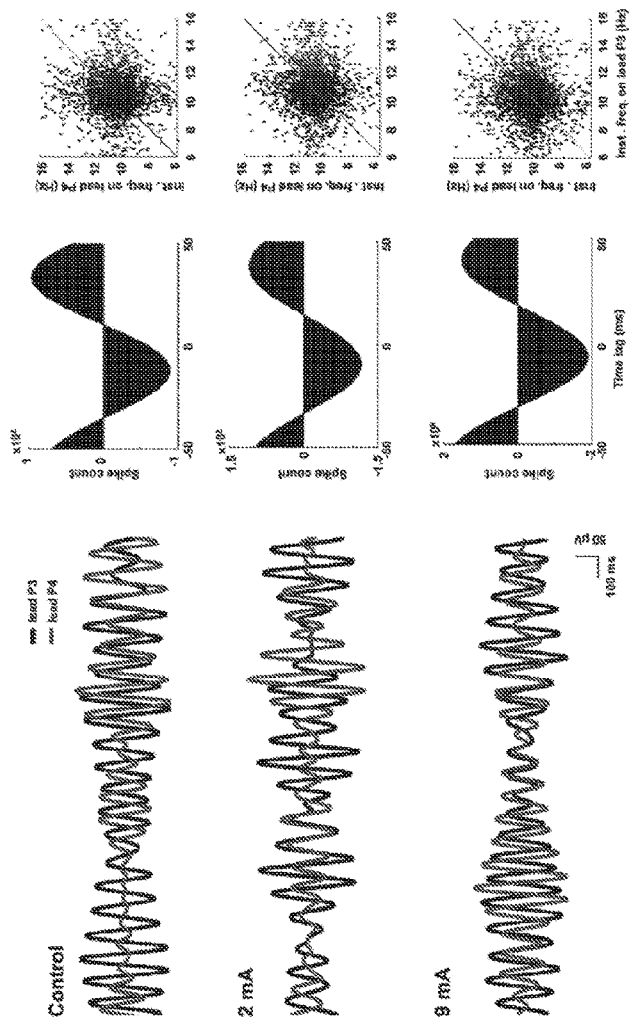
FIG. 6A illustrates alpha-band filtered EEG signals recorded by the occipital leads bilaterally (left panels). Note that the phase and amplitude of alpha waves vary under control and ISP stimulation (2 mA and 9 mA) conditions, suggesting that the traces are substantially free of common electrical artifacts. Time-lag of cross-correlogram peaks is also similar under control and ISP stimulation conditions. Instantaneous frequencies of the EEG traces from the two hemispheres vary from event to event. Note that stimulation-induced artifacts are expected to have constant phase and amplitude ratios at all recording positions.
Figure 6C:
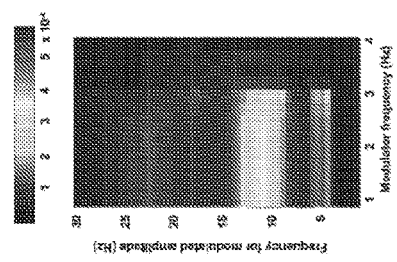
FIG. 6C illustrates representative examples of frequency amplitude coupling reveal stimulus phase modulation of the amplitude of alpha waves.

Further experiments were performed on 19 healthy subjects using currents up to 7.5 mA of ISP stimulation (FIG. 1). A circular array of 12 epicutaneous stimulation electrodes (six on each side) was placed around the head. Each stimulation site consisted of a 0.9% NaCl solution-soaked sponge square connected to 2×3 cm copper mesh. Scalp EEG was monitored by a 2-site montage (P3, P4). In each session, a one minute baseline recording was followed by a train of 1-Hz sinusoids with increasing and decreasing intensity (0, 1.5, 3, 4.5, 6, 7.5, 6, 4.5, 3, 1.5, 0 mA) for 12 seconds, repeated 60 times for each subject, and an additional one minute recovery session. Stimulation artifact generated by the 1 Hz modulator wave of the high frequency pulses was removed by an offline subtraction of a stimulus triggered moving average. The artifact-removed signal preserved the major features of the unstimulated control brain activity, as demonstrated by the non-zero peaked cross correlograms (i.e. phase-independent) and the weakly correlated instantaneous frequencies in the alpha band between the two EEG channels (FIG. 6A).

Figures 4A, 4B, 4C:
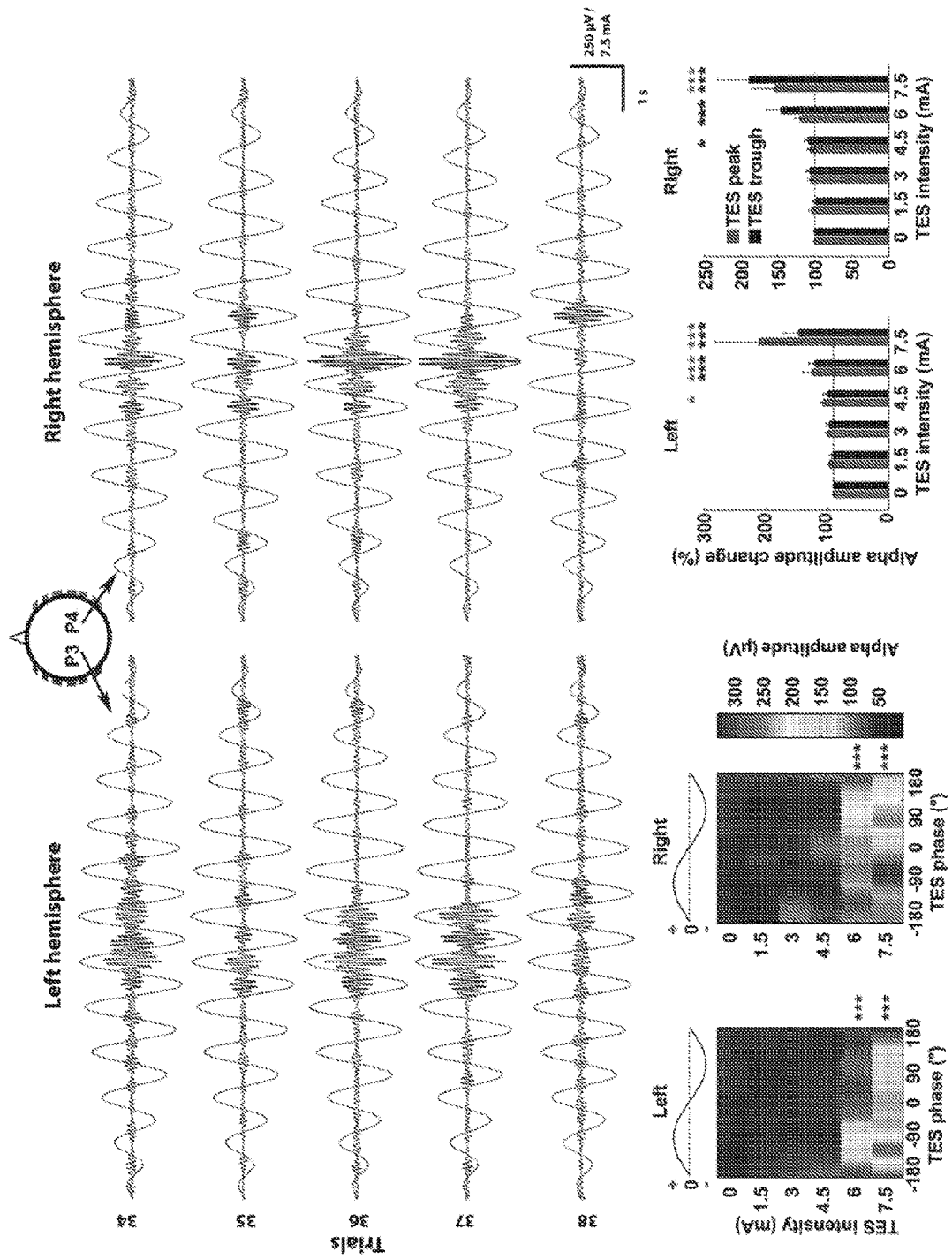
FIG. 4A shows five consecutive example trials of EEG recordings demonstrating alpha amplitude increase for high-intensity ISP stimulation. Grey sinusoids denote the ISP stimulus epoch with an increasing-decreasing amplitude.
FIG. 4B shows phase modulation of the alpha amplitude by ISP stimulation for the entire session from the same subjects as shown in a, showing intensity-dependent alpha amplitude increase (mean across phases are tested in n=45 trials against 0 mA condition, P<0.005 for 6 and 7.5 mA). Note the alternating phase modulation of the left and right hemisphere-derived EEG signals at 6 and 7.5 mA intensities. Intensity maps show the phase-dependent median alpha amplitudes.
FIG. 4C shows a population analysis for the left and right hemispheres, respectively, revealed an intensity-dependent effect. Alpha amplitudes at stimulus peaks and troughs were generally unchanged for stimulus intensities below 4.5 mA. In response to anodal currents in the same hemisphere, phasic modulation was significant at 4.5, 6 and 7.5 mA. In response to cathodal stimulation in the contralateral hemisphere, significant effects were observed only at 7.5 mA (right hemisphere) or 6 and 7.5 mA (left hemisphere) (n=1025 trials from 18 subjects, all intensities tested against 0 mA condition).

A 4.5 mA stimulation or higher at 1 Hz induced various subjective effects, including a subjectively tolerable level of tingling and burning feeling of the skin. Onset and especially the offset of stimulation triggered phosphenes. Subjective feeling of head-movement and horizontally oscillating light in the visual field at the frequency of the stimulation was consistently reported even though the eyes were closed and testing was performed in semi-darkness. Feeling of a moving noise source in the horizontal plane at 1 Hz was present in some subjects at the highest intensities. At high intensities, each subject reported feeling of "metal taste" in the mouth. All subjective effects were stronger at the beginning of the stimulation and attenuated, but did not disappear, during the course of stimulation. No subjective or objective aftereffects were reported after the termination of the stimulation. FIG. 4A is showing five consecutive repetitions of the 12-second long stimulation in a subject. 12-16 Hz filtered (alpha rhythm, endogenous brain activity) EEG signals from the left and right hemisphere (colored traces) have a clear increase in amplitude only when the ISP stimulation is reaching high amplitudes (gray traces).

Figure 6B:
FIG. 6B illustrates that ISP stimulation-induced increase of alpha power was stable throughout the recording epoch, as shown by the similar values during the first and second halves of the seven minute-long stimulation sessions.

TES phase modulation of the amplitude of alpha waves was visible on the filtered signal at high ISP intensities (6 and 7.5 mA; FIGS. 4a and 4b). The LFP modulation was present in both hemispheres and alternated in phase, due to the shifting of the anodal-cathodal current direction (compare epochs in FIGS. 6a and 6b). For group statistics, the mean alpha amplitudes around the stimulus peak (−135 to −45°) and around the stimulus trough (45 to) 135° were measured separately at P3 and P4 at each current intensity. Significant modulation of the LFP amplitude by the TES phase was observed at current intensities of 4.5, 6 and 7.5 mA at each hemisphere when the preferred current direction was applied (FIG. 4C).

For a more detailed analysis, the following current steps (tACS) of ISP stimulation were used in three additional subjects for seven minutes each: 0, 2, 4.5, 7 and 9 mA. No significant effect on alpha rhythm power was observed at 2 mA or 4.5 mA ($P>0.05$; 7 and 5 sessions, respectively), except in one subject with short hair at 4.5 mA ($P<0.05$). At 7 mA and 9 mA, alpha power increased significantly in each subject ($P<0.05$; 11 and 5 sessions, respectively). Alpha power varied as a function of the phase of TES for 4.5, 7 and 9 mA. To examine whether the subjective reports of habituation to the stimulation can be explained by a decreasing effect on network activity, the increased alpha power in the first and second halves of the 7-min stimulation periods were compared. No systematic change in alpha power or any other part of the EEG spectrum across the continuous stimulation (FIG. 6B) was discovered that could explain the subjective habituation.

Neuronal excitability is largely determined by ionic conductances brought about by neurotransmitter-induced postsynaptic potentials. However, neurons can also sense electric fields. Because of the additive nature of the two polarizing mechanisms, theoretically no "minimum effective threshold" of the induced electric field exists. When a neuron is about to emit a spike, very small amounts of fields can bias spike threshold. Thus, when the $V_m$ of a neuron is known, very weak but perfectly-timed forced field can maximize the neuron's response. Endogenous brain rhythms are like a roller coaster, there are 'up' phases when the neurons are excitable, and 'down' phases of the rhythm when they are suppressed and it is the hardest to make them become active. As used herein, "perfectly-timed" refers to the moment when the neuron is the most excitable, i.e., it is the most depolarized by the endogenous inputs (other neurons). In vitro experiments have shown that coupling an oscillatory field to intracellularly generated oscillation can be effective with as small as 0.2 mV/mm gradient. However, to exert a reliable and reproducible impact at any arbitrary moment on local networks, the discharge behavior of at least a fraction of neurons with common targets should be temporally coordinated by some mechanism. In vivo intracellular recordings revealed that electric fields as weak as 1 mV/mm can exert measurable effects on spikes. However, several times more currents were needed to affect native network rhythms, likely because the applied field has to compete with the influence of the large non-affected members of the oscillating network. To place such weak forced fields into perspective, coherently active neurons during physiological operations can generate approximately 2-4 mV/mm gradient across the CA1 pyramidal layer during theta oscillations in the hippocampus and during slow oscillations in the neocortex. Intrinsically generated fields can exceed 10 mV/mm locally during physiological sharp waves and during epileptic activity these values can increase an order of magnitude.

It is important to emphasize that despite the relatively large coverage of the brain volume with multiple recording electrodes, finding the absolute lowest threshold of induced fields is not straightforward. The requirements of affecting some neurons occasionally versus effectively and consistently biasing neuronal circuits (which is required in some applications e.g., reliably terminating epileptic seizures as quickly as possible) are different. Given the complex paths of current spread in the brain and the importance of neuronal geometry in sensing fields, the absence of an effect in any experiment cannot be taken as evidence for absence of effects on a few neurons. Whether such weak effects can have beneficial or deleterious effects on brain function can only be determined by targeted recordings and additional behavioral measures.

Although computational methods have become increasingly sophisticated over the years, the paucity of experimental data makes the justification of models difficult. While subdural measurements can be useful, they measure fields tangentially to the cortical surface, whereas the largest voltage gradients are oriented orthogonal to the cortical surface. Using scalp, cranial and epidural stimulation electrodes and multiple recording electrodes, the three-dimensional spread of electric fields in both rodents and human cadavers were recently quantified by the inventors. The inventors' findings confirm the largely ohmic nature of current spread in the brain, skull and the surround soft tissue. The scalp, subcutaneous tissue and muscles function as an effective shunt, resulting in at least 50% reduction of current spread. The resistance of the skull attenuates the current flow further by another 20-30%, depending on the thickness of the skull. Given the importance of these attenuating factors, the amount of soft tissue, hair and skull thickness should be taken into account in estimating the effective current reaching the brain, and variation of these factors alone may explain the large individual variability of the effectiveness of transcutaneous electric stimulation.

The concept of focusing intensity at circumscribed volumes of tissue is well established by radiological techniques such as cranial stereotactic radiosurgery. In contrast to radiation, simultaneously applied electric fields cannot be focused because of the common conductive media. Instead, the ISP exploits the time integrating property of the neuronal membrane (i.e., the membrane time constant of neurons at ~10 ms), by applying short and spatially rapidly changing sequential fields to establish spatial selectivity. Using ISP, the highest integral of transmembrane charge in neurons develop where successively induced electric fields multiple 'beams' intersect. The more 'beams' are used, the smaller the adverse effects are on other areas traversed by the 'beams.' Using just three rotating dipoles in rats, it was demonstrated that transcranially applied sequential short pulses were able to focus electric fields in one hippocampus sufficiently so that montages targeting the two hemispheres selectively activated (or suppressed) single neuron firing.

The negligible artifacts produced by the ISP technique allowed for direct examination of the impact of scalp stimulation on brain waves in human volunteers. In line with the prediction from the cadaver experiments and the estimated 'minimum' fields (~1 mV/mm) in rodents to affect network activity, alpha power in the occipital areas was affected starting at 4.5 mA and consistent effects in each subjects were shown at >7 mA currents, including amplitude modulation of alpha power as a function of phase of the 1 Hz cyclic field.

Measurements on Rats

Altogether 16 female Long-Evans rats (350-450 g) were implanted with custom-made recording and transcranial stimulating electrodes under urethane anesthesia (1.3-1.5 g/kg, i.p.) for the extracellular recording experiments. After anesthesia induction atropine (0.05 mg/kg, s.c.) was administered to reduce salivation, and the rectal temperature was kept constant at 36-37° C. with a DC temperature controller (TMP-5b; Supertech). Stages of anesthesia were maintained by confirming the lack of vibrissae movements and nociceptive reflex. Skin of the head was shaved and the remaining fur was completely removed by using depilatory cream.

Measuring the Spatial Selectivity of Focused ISP Stimulation in Rats

Two custom designed stimulation strips were 3D printed and glued on the surfaces of the temporal bones bilaterally. Each of the two symmetric strips (width 13 mm, height 3.3 mm and wall thickness 0.7 mm) consisted of 5 individual pockets which were separated from each other by 3.7, 2.2, 2.2 and 3.7 mm (FIG. 2B), and their medial surfaces were resembling the temporal bone curvature of an MRI data based 3D model of a rat skull. The middle pockets were positioned at 5.16 mm posterior from Bregma. Two silicon probes were implanted at 5.16 mm posterior from Bregma and 4 mm lateral of the midline, in the CA1 regions of the hippocampi at both sides. ISP stimulation was performed in current controlled mode using the custom made electronics described below.

Experiments on Human Subject

Stimulation Methods

Epicutaneous stimulating sponge electrodes for ISP were prepared from a 2×3×1.5 cm sponge glued to a 2×3 cm copper mesh, and glued to a rubber band with the sponges inside, keeping approximately 2.5 cm distances between sponges. The rubber band with the twelve electrodes were soaked in 0.9% saline solution and tightened gently around the head. In another embodiment flexible copper foils of the same size as above were glued on the 'skin' surface of the sponges, and the sponges were kept dry. Conductivity was further improved in both cases by putting electrode gel between the wet sponges or the copper foil and the skin. Sinusoid or DC stimulus waveforms were produced by an isolated stimulus generators, either in constant current mode or constant voltage mode. For DC stimulations, commercially available Ag/AgCl electrodes (D=10 mm) were attached to the scalp with electrode gel and a rubber band. For traditional large electrode TES configurations, 10 cm-by-10 cm large sponge electrodes were used.

Experimental Paradigms in Human Subjects

All behavioral tests were performed in semi-darkness in a noiseless environment, following a 30 minute long accommodation period. Stimulus sets for visually evoked potentials (VEP) and steady-state VEPs were played as a movie with 60 or 50 frame/s speed. The monitor refresh rate was adjusted to match the playback rates. Frame changes were monitored by a photodiode attached to the top-right edge of the monitor, where an alternating black-white square marked the consecutive frames. The photodiode signal was recorded in parallel with the EEG signals. The monitor was positioned approximately 15-20 cm in front of the subjects to observe the screen with both eyes. For VEP stimulation a full-screen, 10-by-10 flipping checkerboard pattern was presented 1200 times. Checkerboard flips took place every 500 ms. Steady-state (also known as multifocal) VEP stimulus was generated with 5 concentric-by-12 circular sectors (60 sectors in total), maximum six segments visible simultaneously. Each stimulus was presented for 3 frames, resulting in a 20 or 16.6 Hz stimulation frequency (for 60 and 50 Hz refresh rate, respectively). 8000 stimuli were presented in each session. tcTES stimulation was alternatingly turned on and off every minute during VEP and ssVEP stimulation. To test whether the electromagnetic radiation of the monitor was picked up by the EEG wires and, therefore, produced VEP-like artefactual responses in the EEG signals, the eyes of the subject was covered by a card board, and the measurements were repeated.

To record brain alpha synchronization, the subject was instructed to relax with closed eyes, and paying attention to his respiration. The effect of electrical stimulation on reaction time was measured by instructing the subjects to push a button after randomly appearing short beep sounds, either with their left or right hands. Auditory stimuli were presented at least 100 times for each hand and ISP targeted hemisphere combination (400 stimuli per subject in total).

Custom Made Electronics

Electronic Circuit for Intersectional Short Pulse (ISP) Stimulation

For the ISP stimulation approach, both positive and negative leads of the stimulus generators were connected to 12-12 'normally closed' type TLP52-4 phototransistors. Bidirectional, ground-independent conductivity was achieved the following way. Two phototransistors were serially coupled through their emitter and collector, and the input signal from the waveform generator was fed into both the emitter and the collector end of the transistor doublet, through two Schottky-diodes, which allowed current flow only to the appropriate member of the doublet, depending on the polarity of the signal. The common segment of transistor doublet was connected to a stimulation electrode on the head. The same circuit was constructed for the other pole of the signal as well. Common driver signal to the LED sides opened all four transistors, but due to the diodes two of them were always floating, while the other two closed the circuit through the head. Six such circuits were used for the six electrode pairs, forming six quadruplets (blocks) of transistors. In rats, only three pairs were used. Blocks were activated in a pseudorandom order by TTL pulses generated by a CD74HC4017 Decade counter (Texas Instruments), driven by a 100 kHz TTL generator (ADG3051C, Tektronix).

In an alternative realization for sessions employing variable ISP intensities in human subjects, the phototransistors and diodes were replaced with ADG412 high-speed analog switches (Analog Devices, Norwood, Mass., USA) and the control TTL signals were generated by a PIC18F4525 (Microchip, Chandler, Ariz., USA) microcontroller and isolated by ADuM1400 (Analog Devices) digital isolators. This latter circuitry was also used for the experiments on rats when we compared the spatial effect of ISP and TES pulses.

Data Analysis

In the human experiments, six pairs of scalp stimulation electrodes were used, reducing the required local current by six-fold. In the application of the ISP method, other numbers of pairs of electrodes may also be used, for example, two pairs, three pairs, four pairs, five pairs, seven pairs, or eight pairs. Although it may be beneficial to maximize the number of electrodes used, a cost-benefit estimation must be made, as the greater the number of electrode pairs, the more focal the effect is, but due to size constraints of the skull/scalp, a size of the electrode must be reduced in order to fit all of the electrodes on the skull/scalp. Smaller electrodes may cause bigger side effects on the skin and/or be more painful when the patient perceives the stimulus because the current density is larger. Still, the effective intensities induced adverse skin effects and vestibular reactions. While it was possible to demonstrate the direct effect of scalp stimulation on brain networks, separation of direct and peripherally mediated indirect effects are of utmost importance in understanding the potential therapeutic mechanisms of tDCS or tACS. The next step in advancing the ISP technique is to increase the number of intersecting dipoles generated by pairs of stimulating electrodes and/or implanting them under the skin to eliminate skin shunting. For example, using a montage of 32 electrodes, a large number of dipoles can be formed to create a circumscribed 3-dimensional intersectional focus or target two or more brain structures while reducing the locally applied currents, potentially below skin sensation threshold. The matching of the electrodes to form an electrode group determines the focal point. In theory, if electrode strips with large number of contact sites are used/implanted, it may not be necessary to use up all contact sites to form the electrode groups. If only a subset is used, there is room for creating various focal points. See the rat experiment's drawing on FIG. 2c, which forms three pairs from the ten contact sites. This allows for the creation, for example, of one configuration focusing to the left hemisphere, and another configuration focusing to the right hemisphere. Combining the 'ground truth' measurements from the human cadaver brain with computational models of the head allows a rationale design of focused electric activation of brain structures.

The ISP method may be applied in many applications. For example, the ISP method may be used for immediate intervention, e.g. in the supervision and termination of epileptic seizures. The ISP method may also be used as a possible treatment of other major neuropsychiatric disorders (e.g., depression or anxiety) by reaching a cumulative effect through repetitive interference with endogenous brain activity patterns ('treatment') across days. Other applications of the ISP method include: post-stroke rehabilitation, enhancement of learning and memory recall, sleep quality enhancement, treatment of post-traumatic stress disorder, neuroscience research, transmission of general alerting signals to the brain in machine-brain interface applications, or any application which is currently targeted with transcranial direct current stimulation (tDCS), transcranial alternating current (tACS), other forms of transcranial electric stimulation methods using electrode pairs, transcranial magnetic stimulation, deep brain stimulation, or peripheral nerve stimulations. The ISP method may also be suitable for electrically stimulating other parts of the body, e.g. spinal cord, hearth, peripheral nerves, skeletal muscles. These lists are illustrative only, and the system and method described herein is not limited to these applications. The ISP method may also be applied using other electrode locations e.g. (but not exclusively) onto the skin surface, into the skin, under the skin, onto the skull, into the skull bone, under the skull, onto the dura mater, below the dura mater, onto the brain surface, into the brain tissue, into the ventricles, or any combinations of these, as the concept of the ISP method i.e. the charge integration of multiple sequential electrical pulses by the neuronal (or glial) cell membranes does not depend on the electrode locations. Different electrode locations may imply the need of different current intensities to reach the desired effect.

The ISP method recognizes that the simultaneous application of multiple electric fields through independent current generators cannot induce a spatially focused effect due to a spatially homogenous conductive medium. See FIG. 5. Instead, the ISP method demonstrates the principle of spatio-temporally rotating intersectional short pulse (ISP) stimulation to spatially focus the effect of TES. The method assumes a charge-integrating mechanism over time. An added advantage of fast pulses (<10 µs duty cycle with at least two times longer pause, depending on the number of electrode pairs) is that their high frequency only minimally affects simultaneous electric recording of local field potentials (LFP) or neuronal spikes (usually 1 Hz-5 kHz; 20 kHz sampling) and it does not saturate recording AC coupled amplifiers even at relatively high intensities. Thus, using the ISP method, it is possible to interact with neuronal and/or glial activity in a spatially and temporally selective manner.

The system and method described above offers a better spatial focusing of the effect generated by non-invasive brain stimulation techniques that are currently available. In addition, the ISP system and method described above allow for the use of larger stimulus current intensities without intolerable effects experienced by the patient such as itching, skin-burning, etc. Differences between the system and method described in this application and the conventional electrical stimulation techniques include 1) the use of small surface electrodes rather than large sponge electrodes, 2) the use of multiple electrodes (e.g., electrode pairs or groups) aligned in a way that the axes of the concurrently active electrodes set to different potentials cross each other at a predetermined focal point, 3) delivering the stimulus waveform in a temporally segmented manner onto the electrodes, by activating two or more electrodes (e.g., a subset of the electrodes) at a time, 4) switching through all available electrodes within less than ten milliseconds, and 5) at any moment, the unused or deactivated electrodes are electrically decoupled from the stimulation circuit to avoid shunting. This list is illustrative only. One of ordinary skill in the art would have understood that other differences may exist between the system and method described in this application and the conventional electrical stimulation techniques.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated. Other substitutions, modifications, changes and omissions may be made in the disclosure's operating conditions and arrangement of the embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

Embodiments of the subject matter and the operations described in this specification can be implemented in digital or analog electronic circuitry, with mechanic or optical switches, or in computer software embodied on a tangible medium, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on one or more computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium may be tangible and non-transitory.

The operations described in this specification can be implemented as operations performed by a data processing apparatus or processing circuit on data stored on one or more computer-readable storage devices or received from other sources.

The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors or processing circuits executing one or more computer programs to perform actions by operating on input data and generating output. The processes and logic flows can also be performed by, and apparatus can also be implemented as, special purpose logic circuitry, e.g., an FPGA or an ASIC.

Processors or processing circuits suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display), OLED (organic light emitting diode), TFT (thin-film transistor), plasma, other flexible configuration, or any other monitor for displaying information to the user and a keyboard, a pointing device, e.g., a mouse trackball, etc., or a touch screen, touch pad, etc., by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

What is claimed is:

1. A system for electrical brain stimulation comprising:
a plurality of electrodes arranged in a plurality of electrode groups, each electrode group comprising two or more electrodes where at least one electrode is set to a different potential level such that a voltage difference is generated between members of an electrode group, the plurality of electrodes configured to be arranged on one of:
an exterior surface of a patient's scalp,
an exterior surface of the patient's skull,
in the patient's skull, on the patient's brain or dura surface, or in the patient's brain; and a ground-independent switching circuit configured to selectively activate and deactivate electrode groups via at least one ground-independent switch;

wherein axes connecting electrodes set to different potential levels within each electrode group or axes of generated electrical fields intersect at one or more predetermined focal points, wherein the ground-independent switching circuit is programmed to sequentially activate and deactivate electrode groups, and wherein the system utilizes the capacitive properties of a neuronal and/or glial cell membrane to implement a charge integrating mechanism, which temporally integrates an effect of multiple independent, sequential electrical pulses delivered through the two or more activated electrodes.

2. The system of claim 1, wherein each electrode in the plurality of electrodes is a member of one or more electrode groups.

3. The system of claim 1, wherein each electrode in the plurality of electrodes is only a member of one electrode group.

4. The system of claim 1, wherein a cycle comprises one activation and one deactivation of each electrode in an electrode group, and a duration of the cycle is 1 to 100 milliseconds.

5. The system of claim 4, wherein each electrode group is activated for shorter than 3.5 ms.

6. The system of claim 4, wherein a pause time between consecutive reactivations of any electrode groups is at least twice as long as the duration of its preceding activation.

7. The system of claim 6, wherein a plurality of high-intensity pulses is perceived by any cell of brain tissue as a smooth, continuous integrative stimulus at the focal point, due to the capacitive properties and consequent temporal integration of the neuronal and/or glial cell membrane.

8. The system of claim 1, wherein a cycle comprises one activation and one deactivation of each electrode in an electrode group, and a duration of the cycle is less than a time constant of the neuronal and/or glial cell membrane.

9. The system of claim 1, wherein the ground-independent switching circuit comprises:

the at least one ground-independent switch, which is configured to connect or disconnect two or more signal lines;

at least one diode; and a commanding circuit configured to drive the at least one ground-independent switch.

10. The system of claim 9, wherein the at least one ground-independent switch comprises a phototransistor.

11. The system of claim 9, wherein:

the ground-independent switching circuit comprises a plurality of ground-independent switches configured to connect or disconnect two or more signal lines, a plurality of diodes, and a commanding circuit configured to drive the plurality of ground-independent switches, the plurality of ground-independent switches comprise a plurality of phototransistors, and each electrode pole is connected to a collector-emitter connection of two serially connected phototransistors.

12. The system of claim 1, wherein the plurality of electrodes comprise a plurality of small surface electrodes.

13. The system of claim 1, wherein the plurality of electrodes comprise a plurality of large sponge electrodes.

14. The system of claim 1, further comprising a current or voltage source.

15. The system of claim 13, wherein an electrode group comprises an electrode pair in which two electrodes are configured such that a first electrode is physically connected either temporarily or constantly to one pole of the current or voltage source, and a second electrode is connected to a second pole of the current or voltage source.

16. A method of electrical brain stimulation comprising;

arranging a plurality of electrodes on an exterior surface of a patient's scalp, an exterior surface of the patient's skull, in the patient's skull, on the patient's brain or dura surface, or in the patient's brain in a plurality of electrode groups, each electrode group comprising two or more electrodes where at least one electrode is set to a different potential level such that a voltage difference is generated between members of an electrode group; and selectively activating and deactivating electrode groups via at least one ground-independent switch, wherein axes connecting electrodes are set to different potential levels within each electrode group or axes of generated electrical fields intersect at one or more predetermined focal points, and wherein the capacitive properties of neuronal and/or glial cell membranes are utilized to implement a charge integrating mechanism, which temporally integrates an effect of multiple independent, sequential electrical pulses delivered through the two or more activated electrodes.

17. The method of claim 16, wherein deactivated electrodes are electrically decoupled from a stimulation circuit to avoid shunting an electrical gradient generated by connected active electrodes.

18. The method of claim 16, wherein a cycle comprises one activation and one deactivation of each electrode in an electrode group, and a duration of the cycle is less than a time constant of the neuronal and/or glial cell membrane.

19. The method of claim 18, wherein the time constant of the neuronal and/or glial cell membrane is 1 to 100 milliseconds.

20. The method of claim 19, wherein each electrode group is activated for shorter than 3.5 ms.

\* \* \* \* \*

UNITED STATES PATENT AND TRADEMARK OFFICE
CERTIFICATE OF CORRECTION

| | | |
|---|---|---|
| PATENT NO. | : 11,452,862 B2 | Page 1 of 1 |
| APPLICATION NO. | : 16/613400 | |
| DATED | : September 27, 2022 | |
| INVENTOR(S) | : Antal Berenyi and Gyorgy Buzsaki | |

It is certified that error appears in the above-identified patent and that said Letters Patent is hereby corrected as shown below:

In the Specification

Column 1, Line 13, following after the "Cross Reference to Related Applications" sub-heading and paragraph, add new sub-heading and paragraph:
STATEMENT OF GOVERNMENT INTEREST
"This invention was made with government support under grant number R01 MH107396 awarded by the National Institutes of Health. The government has certain rights in the invention."

Signed and Sealed this
First Day of April, 2025

Coke Morgan Stewart
*Acting Director of the United States Patent and Trademark Office*